US00PP12673P2

(12) United States Plant Patent
Cully

(10) Patent No.: US PP12,673 P2
(45) Date of Patent: Jun. 4, 2002

(54) OAK TREE NAMED 'LONG'

(76) Inventor: Earl Cully, R.R. 5, Box 84A, 846 Hoagland Rd., Jacksonville, IL (US) 62650

( * ) Notice: Subject to any disclaimer, the term of this patent is extended or adjusted under 35 U.S.C. 154(b) by 0 days.

(21) Appl. No.: 09/007,695

(22) Filed: Jan. 14, 1998

(51) Int. Cl.[7] ..... A01H 5/00
(52) U.S. Cl. ..... Plt./225
(58) Field of Search ..... Plt./225

(56) References Cited

U.S. PATENT DOCUMENTS

PP6,539 P * 1/1989 Astes, Jr. ..... Plt./225

OTHER PUBLICATIONS

Green, T–L., Hess, W.J. Two New Hybrid Oaks (*Quercus–Ragaceae*) *J. International Oak Society*, No. 8 pp 16–20 (Summer, 1998).

Huxley et al., The New Royal Horticultural Society Dictionary of Gardening, vol. III, p. 787, The Stockton Press, 1992.*

* cited by examiner

*Primary Examiner*—Bruce R. Campell
*Assistant Examiner*—Kent L. Bell
(74) *Attorney, Agent, or Firm*—W. Dennis Drehkoff; Ladas & Parry

(57) ABSTRACT

A new and distinct cultivar of an oak tree exhibiting an upright growth habit, extreme winter hardiness, strong-wooded, dark green foliage and is highly resistant to powdery mildew.

4 Drawing Sheets

The present invention comprises a new and distinct cultivar of hybrid oak tree, botanically known as *Quercus robur* 'Fastigiata'×*Quercus bicolor*, and referred to by the cultivar name 'Long'.

The initially discovered tree is growing in a cultivated area on the home grounds of inventor Earl Cully, on Rural Route #5, Box 84A, 846 Hoagland Road, eight miles south of Jacksonville, Ill., in Morgan County, in Township 14, Range 10.

The new cultivar 'Long' is the result of seed collected in the fall of 1974, from a tree of *Quercus robur* 'Fastigiata' that had been pollinated by an unnamed tree of *Quercus bicolor* (as determined by Dr. Gary Booth, Dept. of Horticulture, University of Missouri, Columbia, Mo.). All seedlings grown from seed collected from this one tree proved to be $F_1$ hybrids. From an approximate one-thousand seedlings, about sixty superior $F_1$ seedlings were selected for further evaluation. Out of the sixty $F_1$ hybrid seedlings, six have proven to be worthy of cultivar status.

This new hybrid exhibits an upright habit of growth, exhibits great hybrid vigor, is extremely winter hardy, is very strong-wooded, has dark green leathery foliage (see FIG. 1), and is highly resistant to powdery mildew.

The new $F_1$ cultivar now named 'Long' has been successfully asexually propagated by chip budding onto *Quercus bicolor*. Bud take has been about 95% with no imcompatibility between scion and rootstock. Buds set on two-year rootstocks have produced six to eight feet of growth in one growing season with lightly branched tops. Asexually propagated trees of this $F_1$ hybrid oak now named 'Long' have maintained the unique characteristics which in combination distinguish 'Long' from other cultivar selections of this $F_1$ hybrid cross, and from either of its parents, *Quercus robur* and *Quercus bicolor.*

1. Compared to *Quercus robur*, this new hybrid is far more winter hardy, withstanding temperatures of −28° to −30° F. without damage. During October 1991, temperatures were warm for the entire month, but on October 31, dropped into the 'teens. On November 3, a record low was recorded of −1° F. Many tree species, including the English oak, were badly damaged from this arctic blast of air, and some were killed to the ground. The new $F_1$ hybrid now known as 'Long' did not suffer the slightest damage from this blast of frigid air. In the twenty-one years that it has been under test, this area has had winter lows of −28° to −30° F. This $F_1$ hybrid did not suffer the slightest damage. Based on these winter lows, this new hybrid would be reliably hardy in Zone 4A and the lower one-half of Zone 4B (USDA Plant Hardiness Zone Map).

2. The new cultivar now named 'Long' is a vigorous grower with an upright habit of growth (see FIG. 2). Its form would resemble that of 'Bowhall' red maple, with a narrow to medium oval crown.

3. The new cultivar now named 'Long' is highly resistant to wind and ice. This hybrid has never had a limb break from wind or ice during the twenty-one years it has been under test. Its staminate parent, an unnamed tree of *Quercus bicolor*, would account for its great strength, as this species has the toughest and strongest wood of any of the oaks.

4. The foliage of the new hybrid now named 'Long' is dark green and leathery in texture (see FIG. 3). It is highly resistant to powdery mildew (see FIG. 3).

5. The new hybrid exhibits hybrid vigor. A chip bud set on a two year *Quercus bicolor* understock will make six to eight feet of growth with a lightly branched top in one growing season.

6. The new hybrid at twenty-one years of age is thirty-five feet in height, with a limb spread of thirteen and one-half feet.

BRIEF DESCRIPTION OF THE DRAWINGS

The accompanying colored photographs illustrate the overall appearance and color of the new hybrid oak tree showing colors as true as is reasonably possible to obtain in colored reproductions of this type. Actual bark and foliage colors may differ from bark and foliage colors in the photographs due to light reflectance.

FIG. 1 shows the cultivar in summer with its dark green highly resistant to powdery mildew foliage with an upright growth habit and narrow to medium oval crown;

FIG. 2 shows the cultivar in the dormant state with its dense branching habit of growth;

FIG. 3 shows a young asexually produced tree exhibiting an upright, narrow to medium growth habit;

FIG. 4 shows the under side of a leaf on the left and the upper side of a leaf on right.

DETAILED BOTANICAL DESCRIPTION

In the following description, color references are made to The Royal Horticultural Society Colour Chart except where general terms of ordinary dictionary significance are used. Trees described were about 21 years old grown in Morgan county, Ill.

THE PLANT

TREE, HYBRID OAK 'LONG'

Name: Cultivar 'Long'.

Parentage: Seedling, 1975.

*Seed parent.*—*Quercus robur* 'Fastigiata'. Patent: none.

*Pollen parent.*—Unnamed tree of *Quercus bicolor*. Patent: none.

Classification: *Quercus robur* 'Fastigiata'×*Q. bicolor*, Hybrid Oak (*Quercus*×*warei*) as described in the Journal of the International Oak Society (No. 8, Summer 1998 Issue, page 19).

Where discovered: At the home of Earl Cully, in a Cultivated area, Morgan County, Ill., Township 14, Range 10.

This plant has been asexually reproduced from: Chip budding on *Quercus bicolor* rootstock. The first act of asexual reproduction was accomplished by chip budding and took place at Heritage Trees, Jacksonville, Ill. Current propagation is by chip budding onto swamp while oak and is currently being performed in Illinois, Minnesota and Oregon.

Form: Tree.

Shape: Cylindrical.

Height: 10.7 m (35').

Spread: 4.2 m (13.67').

Trunk size: 27.5 cm (10.8") which is the diameter of the tree at breast height 1.3 m above ground level.

Base: Cylindrical.

Bark: Bark gray-green (197A, 198A, 198B, 198D, R.H.S.); small rectangular blocks, size 1.2–2.5 cm in length (0.5–1.0"); vertical alignment, thin; slight exfoliation.

Growth rate: Moderate to fast, depending on site.

Strength: Excellent.

Branches:

*Angle of attachment.*—Most branches 60 and 70° with a range from 45 to 80° from the main trunk.

*Spacing.*—Dense.

*Bark.*—Greenish-gray, exfoliating, more silver-gray beneath exfoliation (R.H.S. 198A, 201A).

*Lenticles.*—Small, scattered not prominent.

Twigs:

*Bark.*—Greenish to brown (R.H.S. 148A to 197A).

*Lenticles.*—Small, scattered white.

*Buds.*—(vegetative) small, 2 mm wide by 3 mm long (191A, 197B R.H.S).

Leaves:

*Length.*—6–18 cm, average 14.4 cm.

*Width.*—3–11.5 cm, average 8.1 cm.

*Form.*—Obovate to obelliptical; base cuneate; apex narrowly to broadly acute.

*Margin.*—Coarsely lobed with 6–8 pairs of entire usually obtuse lobes.

*Texture.*—Leathery; glossy; glabrous above, velevety tomentose beneath.

*Quantity.*—Abundant.

*Color.*—Upper side: dark green (139B). Under side: (194B).

*Petioles.*—Length 0.5–1.5 cm, average 0.7 cm, color is 149C.

*Ribs and veins.*—6–8 pairs (149C R.H.S.) (See FIG. 4).

Buds: (Vegetative) small (2 mm wide by 3 mm long), blunt, reddish-brown (191A, 197B R.H.S.) bud scale margins with irregular tufts of hair.

Flowers: Staminate: Typical of the species.

Seeds: Somewhat sparsely produced; single or double on mostly glabrous peduncles 3.5–7.5 cm long; acorns broadly ovoid to elliptical, 19–26 mm long×14–18 mm diameter; exposed shells are covered with a white tomentum, becoming slightly glabrate; capsules hemisphere, 13–66 mm length×20–24 mm diameter, covering up to ½ of the acorn, watery rhomboid scales covered with velvety tomentum. Color: acorn 165B to 165C, capsules 156A with tinge of 164C.

Disease resistance: Trees growing in Jacksonville, Ill., Barrington, Ill., and Portland, Oreg. have exhibited a strong resistance to powdery mildew.

It is claimed:

1. A new and distinct cultivar of Hybrid Oak tree named 'Long' as illustrated and described.

* * * * *

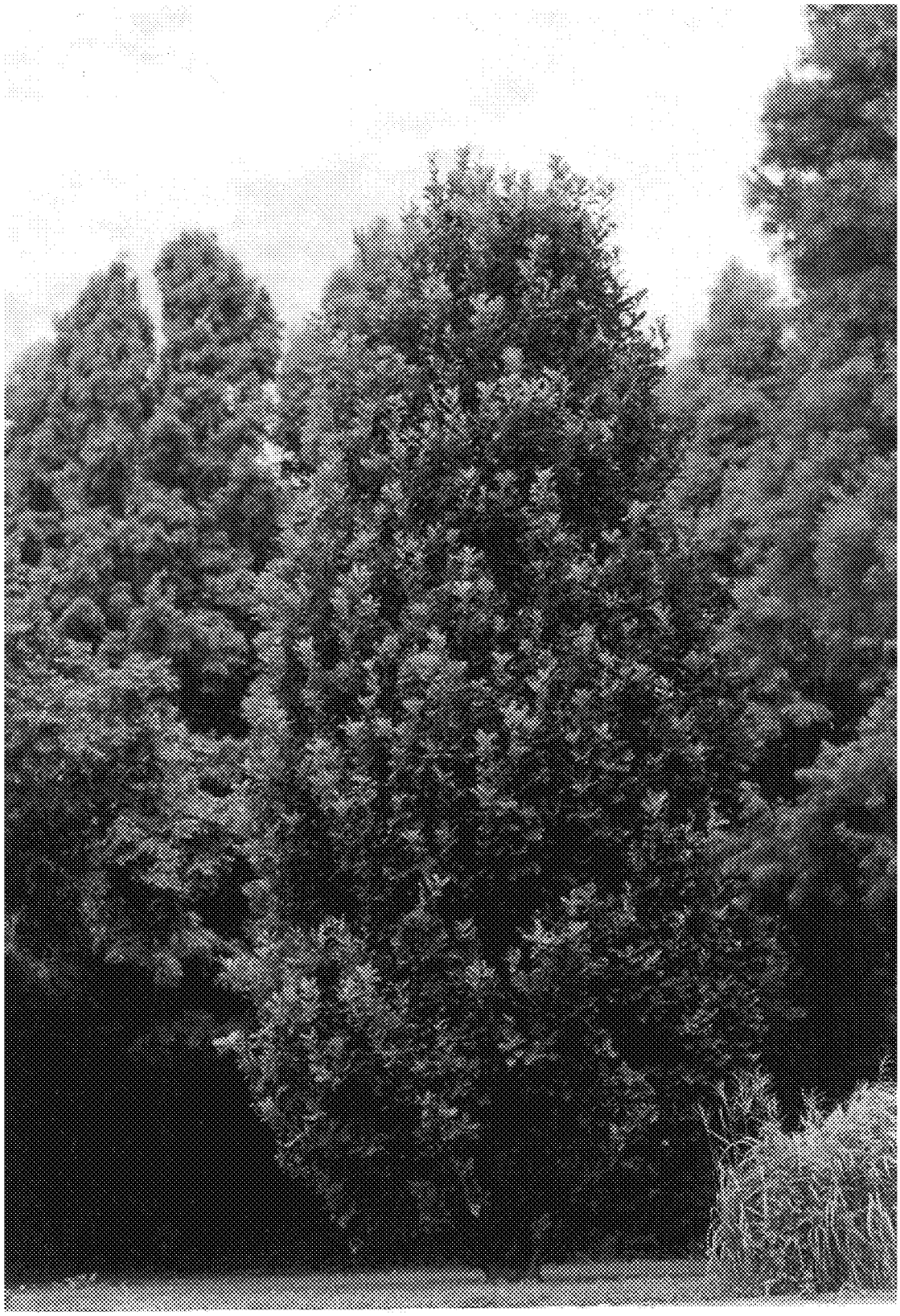
Fig. #1

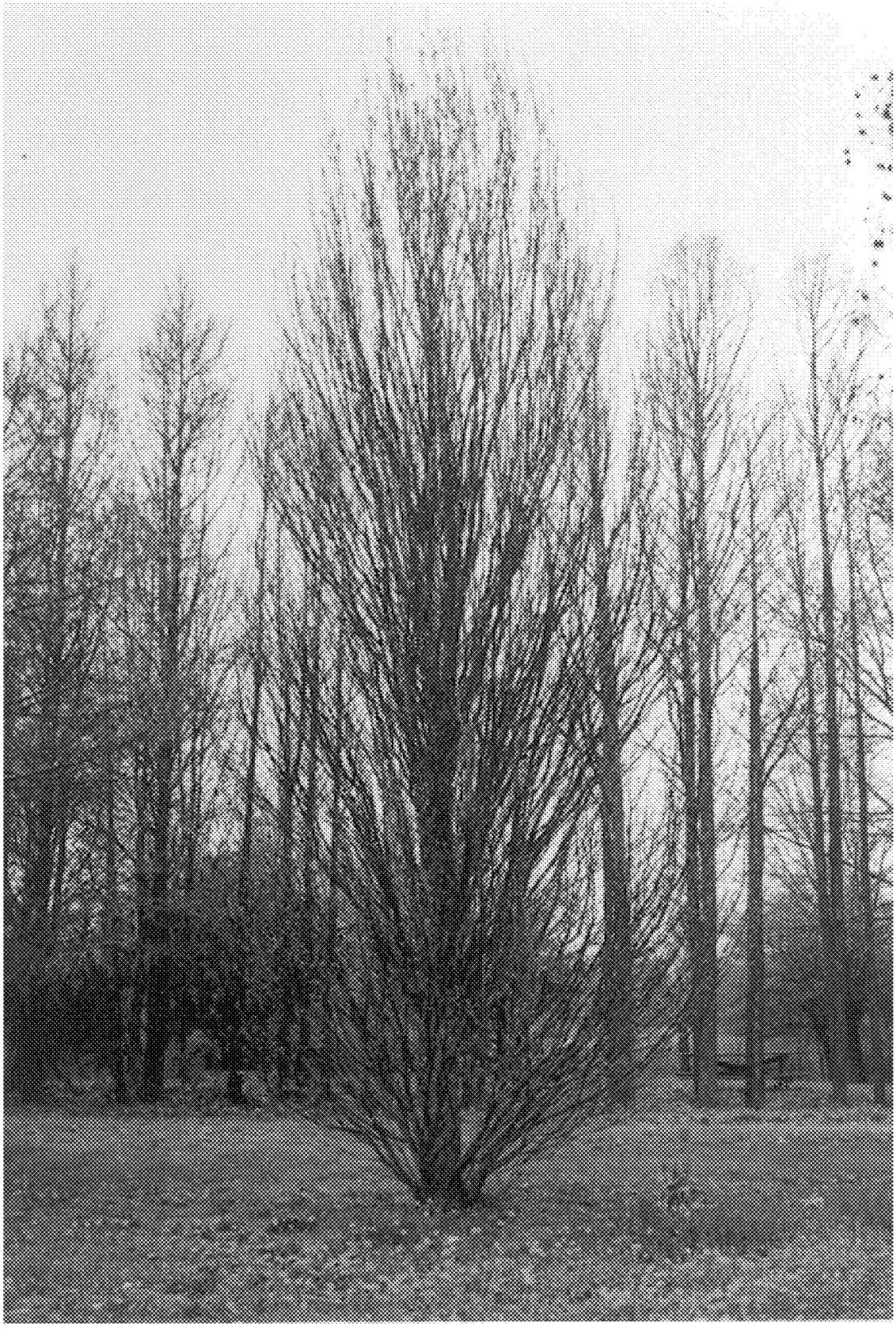
Fig. #2

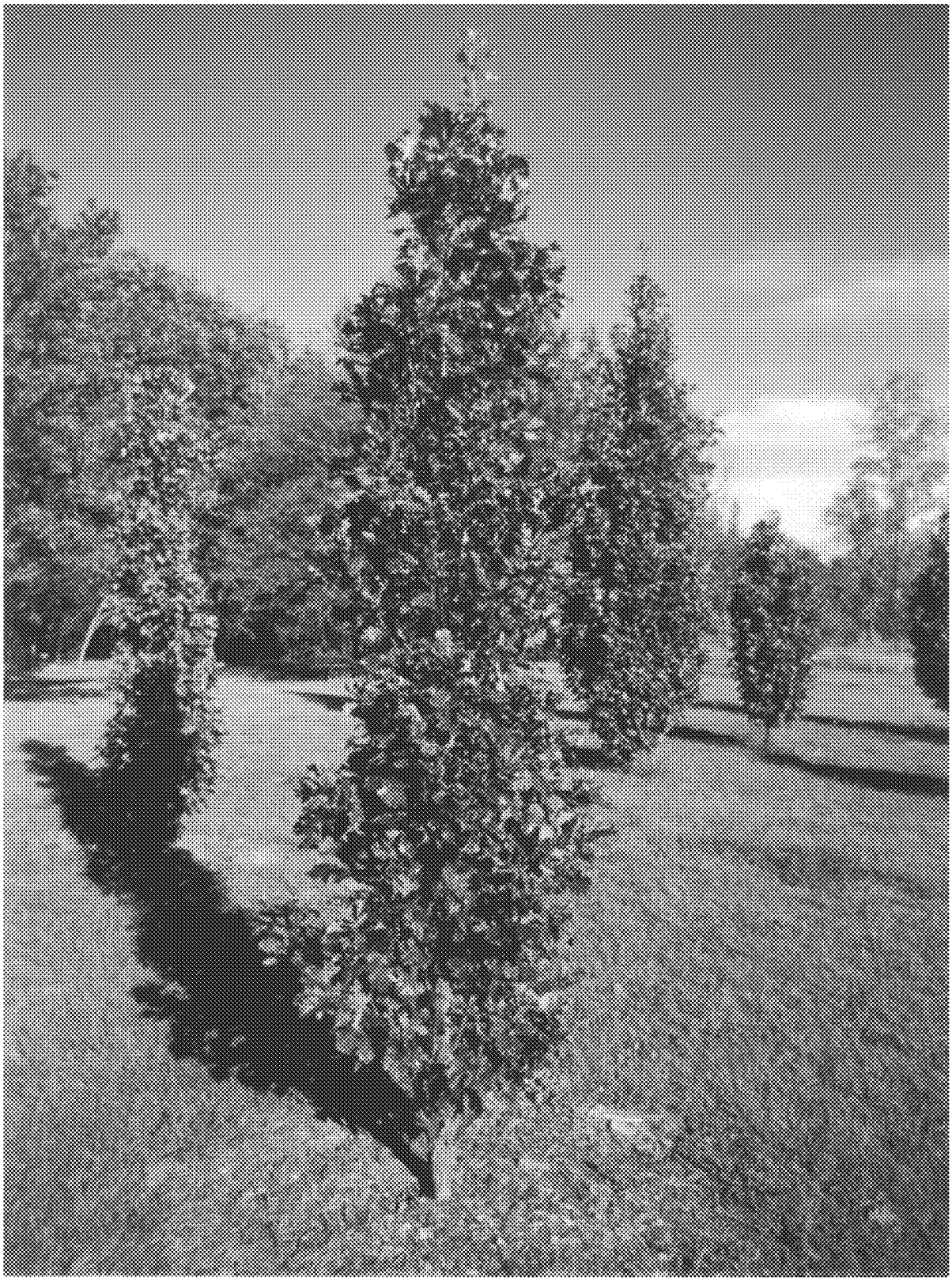
Fig. #3

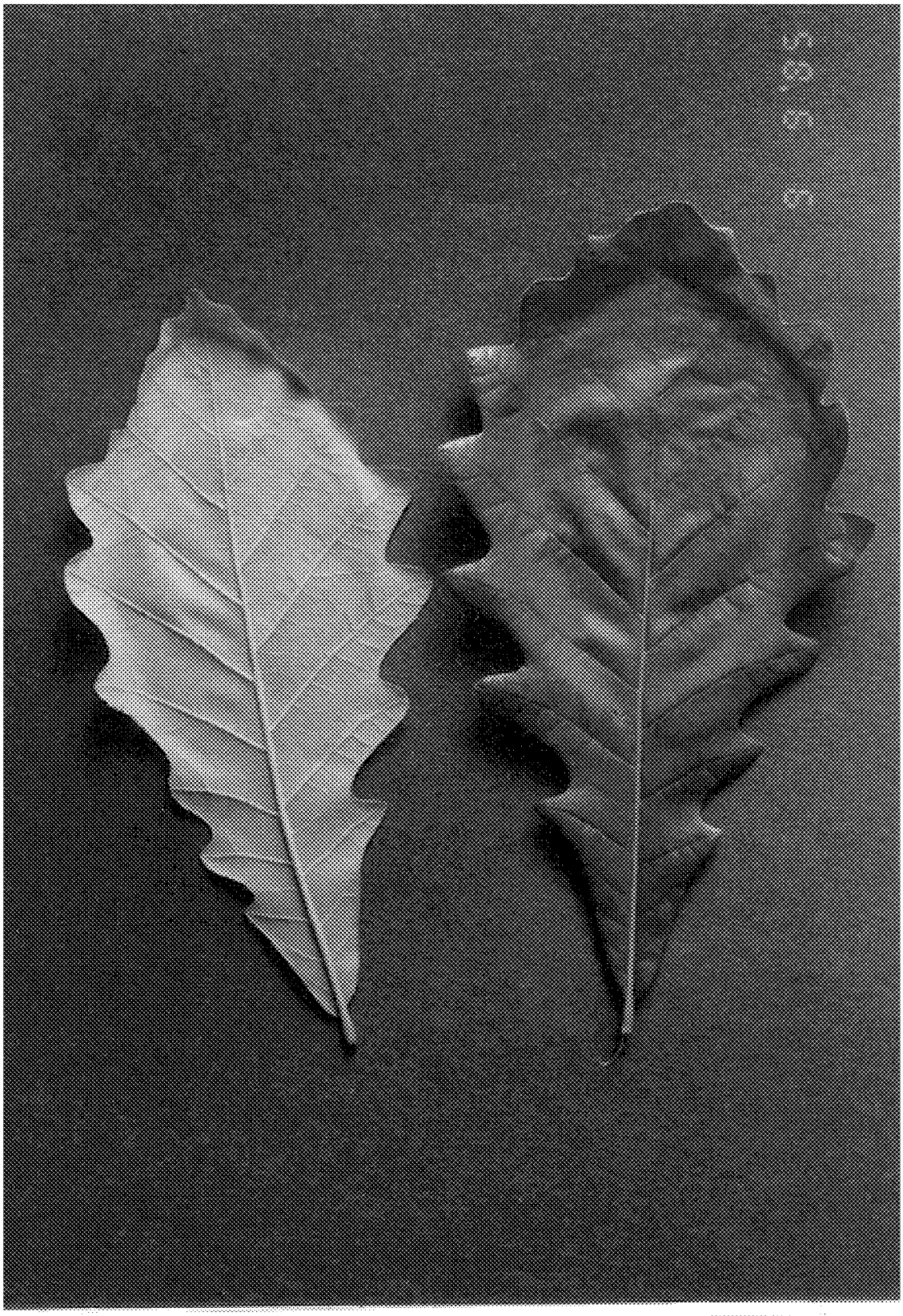
Fig. #4

UNITED STATES PATENT AND TRADEMARK OFFICE

CERTIFICATE OF CORRECTION

PATENT NO. : PP 12,673 P2
DATED : June 4, 2002
INVENTOR(S) : Earl Cully

It is certified that error appears in the above-identified patent and that said Letters Patent is hereby corrected as shown below:

Title page,
Column 1,
Lines 26-27, delete “imcompatibility” and insert -- incompatibility --;

Column 3,
Line 33, delete “while oak” and insert -- white oak --;

Signed and Sealed this

Third Day of June, 2003

JAMES E. ROGAN
*Director of the United States Patent and Trademark Office*